(12) United States Patent  
Betzold (10) Patent No.: US 8,583,233 B2  
(45) Date of Patent: Nov. 12, 2013

(54) MODIFICATION OF AV CONDUCTION TIME SAMPLING RATE

(75) Inventor: Robert A. Betzold, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 115 days.

(21) Appl. No.: 13/193,735

(22) Filed: Jul. 29, 2011

(65) Prior Publication Data

US 2013/0030486 A1 Jan. 31, 2013

(51) Int. Cl.
*A61N 1/365* (2006.01)

(52) U.S. Cl.
USPC .......... 607/18; 607/2; 607/9; 607/17; 607/19; 607/25; 607/30

(58) Field of Classification Search
USPC ................... 607/9, 17–19, 6, 25, 30
See application file for complete search history.

(56) References Cited

U.S. PATENT DOCUMENTS

| | | | |
|---|---|---|---|
| 5,117,824 A | 6/1992 | Keimel et al. | |
| 5,372,607 A * | 12/1994 | Stone et al. | 607/30 |
| 5,425,750 A | 6/1995 | Moberg | |
| 5,725,561 A | 3/1998 | Stroebel et al. | |
| 5,861,007 A | 1/1999 | Hess et al. | |
| 6,507,756 B1 | 1/2003 | Heynen et al. | |
| 6,571,121 B2 * | 5/2003 | Schroeppel et al. | 600/515 |
| 6,792,307 B1 | 9/2004 | Levine et al. | |
| 7,292,168 B2 * | 11/2007 | Wesselink et al. | 341/123 |
| 7,395,113 B2 | 7/2008 | Heruth et al. | |
| 7,593,773 B2 | 9/2009 | Boute et al. | |
| 7,643,878 B1 | 1/2010 | Muller et al. | |
| 7,869,872 B2 | 1/2011 | Sheldon et al. | |
| 2004/0215262 A1 | 10/2004 | Ferek-Petric | |
| 2005/0209512 A1 * | 9/2005 | Heruth et al. | 600/301 |
| 2006/0167508 A1 * | 7/2006 | Boute et al. | 607/9 |
| 2007/0191892 A1 | 8/2007 | Mullen et al. | |
| 2010/0305647 A1 * | 12/2010 | McCabe et al. | 607/18 |
| 2013/0030489 A1 * | 1/2013 | Munsterman et al. | 607/25 |

OTHER PUBLICATIONS

U.S. Appl. No. 13/193,747, filed Munsterman et al.

\* cited by examiner

*Primary Examiner* — Scott Getzow
*Assistant Examiner* — Christopher A Flory
(74) *Attorney, Agent, or Firm* — Carol F. Barry

(57) ABSTRACT

Methods and/or devices for modifying the sampling rate for measuring a patient's intrinsic AV conduction time during cardiac therapy. For example, the sampling rate for measuring a patient's intrinsic AV conduction time may be modified (e.g., decrease or increased) based on one or more monitored physiological parameters, such as activity level and/or heart rate.

20 Claims, 7 Drawing Sheets

MODIFICATION OF AV CONDUCTION TIME SAMPLING RATE

The disclosure herein relates to measuring a patient's intrinsic atrioventricular (AV) conduction time during cardiac therapy (e.g., cardiac resynchronization therapy), and further to devices for performing and implementing such methods.

Cardiac therapy devices (e.g., an implantable medical device (IMD) for performing cardiac resynchronization therapy (CRT)) may provide cardiac therapy (e.g., pacing therapy) and may employ a programmable fixed AV delay in combination with a rate adaptive AV delay feature which adjusts the AV delay based on one or more monitored physiological parameters (e.g., sensed activity such as atrial events, ventricular events, etc.). For example, a cardiac therapy device may periodically measure a patient's intrinsic AV conduction time, or interval, and adjust the timing of right ventricular (RV) and left ventricular (LV) pacing pulses in response to the measured intrinsic AV conduction time, e.g., to optimize cardiac functionality. A patient's intrinsic AV conduction time is the time between an atrial (e.g., right atrium) event (e.g., atrial pace or intrinsic atrial event (depolarization)) and an intrinsic ventricular (e.g., right ventricle) event (depolarization). As used herein, an "intrinsic" ventricular event or conduction is one that occurs or is conducted naturally.

For example, a CRT algorithm (e.g., performed by an IMD) may measure a patient's intrinsic AV conduction time once every minute by forcing delays used for ventricular pacing, such as the paced AV delay (PAV) and the sensed AV delay (SAV), to a long value (e.g., 300 milliseconds (ms), 350 ms, etc.). The PAV is an adjustable time period between a paced atrial event and an optimally paced ventricular event (e.g., where a device may optimally deliver a ventricular pace), and the SAV is an adjustable time period between a sensed atrial event and an optimally paced ventricular event. Conventionally, the intrinsic AV conduction time measurement has been performed periodically (e.g., every 60 seconds) so that the CRT algorithm can adapt to changes in the patient's intrinsic AV conduction time.

Figure 7:
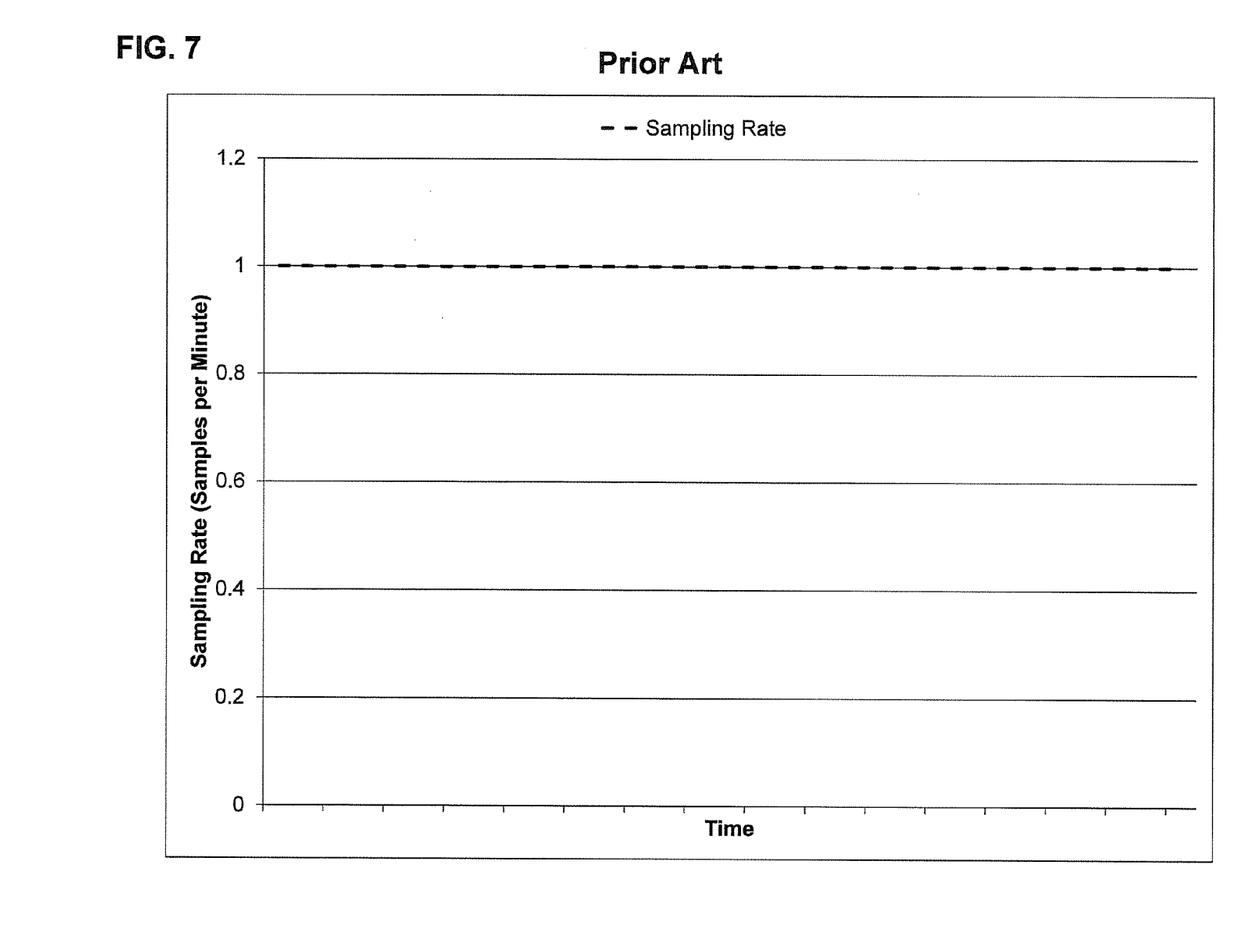
FIG. 7 is a graph displaying an intrinsic AV conduction time sampling rate, e.g., used by an IMD in the delivery of cardiac therapy, over time.

The rate at which the intrinsic AV conduction time is measured may be referred to as an intrinsic AV conduction time sampling rate. For example, if the intrinsic conduction time measurement periodically occurs every 60 seconds, the intrinsic AV conduction time sampling rate is one sample per 60 seconds, or one sample per minute. As described, CRT algorithms and IMDs generally utilize a fixed intrinsic AV conduction time sampling rate, such as one sample per minute. An intrinsic AV conduction time sampling rate of 1 sample per minute, e.g., for use by an IMD delivering cardiac therapy, is plotted over time in FIG. 7. As shown, the intrinsic AV conduction time sample rate is constant or unchanging over time.

SUMMARY

Exemplary methods and/or devices described herein may reduce the number of intrinsic AV conduction time measurements while maintaining a desired response time to changes in the patient's intrinsic AV conduction time. For example, the intrinsic AV conduction time measurement may be performed less often (e.g., at a lower sample rate) when the patient's activity level is constant or stable (e.g., long periods of being at rest or exercise), and more often (e.g., at a higher sampler rate) when a change in the patient's activity level is detected. In other words, the sampling rate at which the patient's intrinsic AV conduction time is measured may be adjusted or modified "on the fly" based on one or more physiological parameters.

Further, for example, a patient's heart rate may be monitored and the intrinsic AV conduction time measurement may be performed less often when the patient's heart rate is constant and more often when the patient's heart rate changes. Still further, for example, the AV conduction time measurement may be performed less frequently when the patient is at rest (e.g., when the need for adjusting may be lower) and more frequently when the patient is not at rest (e.g., when the need for adjusting may be higher). Still further, for example, the intrinsic AV conduction time measurement may be performed less often but a patient profile may be generated (e.g., within an IMD) that maps the patient's heart rate (or sensor rate) to desired device AV intervals, and the generated profile may be utilized to pace the patient's heart based on the patient's heart rate (e.g., which is mapped to the patient's intrinsic AV conduction time in the profile) and/or modify the intrinsic AV conduction time sampling rate (e.g., decrease the sampling rate when a strong correlation exists in the profile between the presently monitored heart rate and intrinsic AV conduction time).

One exemplary implantable medical device disclosed herein for use in delivering cardiac therapy to a patient may include sensing apparatus configured to monitor physiological parameters of a patient (e.g. the sensing apparatus may include at least one electrode to monitor electrical activity of the patient's heart), a therapy delivery module configured to deliver cardiac therapy to the patient, and a control module coupled to the sensing apparatus and to the therapy delivery module. The control module may be further configured to monitor one or more physiological parameters of a patient, periodically sample the patient's intrinsic atrioventricular (AV) conduction time at a sampling rate for use in determining one or more pacing parameters (e.g., a sampling rate that is greater than zero), and modify the sampling rate based on the monitored one or more physiological parameters.

The exemplary device may further include therapy apparatus coupled to the therapy delivery module and configured to deliver cardiac therapy to the patient. Further, the control module may be further configured to determine an optimal AV delay for use in pacing the patient's heart based on the patient's sampled intrinsic AV conduction time and pace the patient's heart using the therapy delivery apparatus based on the determined optimal AV delay.

In at least one embodiment of the exemplary devices described herein, the control module may be further configured to determine the patient's activity level based on the monitored one or more physiological parameters, increase the sampling rate if a change in the patient's activity level is detected, and/or decrease the sampling rate if the patient's activity level is stable over a selected period of time. For example, the control module may be further configured to monitor the patient's motion and determine the patient's activity level based at least on the patient's motion monitored over a selected period of time.

In at least another embodiment of the exemplary devices described herein, the control module may be further configured to monitor the patient's heart rate, increase the sampling rate if a change in the patient's heart rate is detected, and/or decrease the sampling rate if the patient's heart rate is stable over a selected period of time.

In at least another embodiment of the exemplary devices described herein, the control module may be further configured to determine whether the patient is resting based on the monitored one or more physiological parameters and decrease the sampling rate if the patient is resting.

In at least another embodiment of the exemplary devices described herein, the control module may be further configured to generate a profile correlating at least one of the monitored one or more physiological parameters to the patient's sampled intrinsic AV conduction time (e.g., a profile that correlates the patient's sampled intrinsic AV conduction time to the patient's heart rate) and modify the sampling rate based on the profile.

One exemplary method disclosed herein for use in an implantable medical device operable for delivery of cardiac therapy to a patient includes monitoring one or more physiological parameters of a patient, periodically sampling the patient's intrinsic atrioventricular (AV) conduction time at a sampling rate for use in determining one or more pacing parameters (e.g., a sampling rate that is greater than zero), and modifying the sampling rate based on the monitored one or more physiological parameters. The exemplary method may further include determining an optimal AV delay for use in pacing the patient's heart based on the patient's sampled intrinsic AV conduction time and pacing the patient's heart based on the determined optimal AV delay.

In at least one embodiment of the exemplary methods described herein, modifying the sampling rate based on the monitored one or more physiological parameters (e.g., the patient's motion) may include determining the patient's activity level based on the monitored one or more physiological parameters (e.g., the patient's motion), and modifying the sampling rate based on the monitored one or more physiological parameters may include increasing the sampling rate if a change in the patient's activity level is detected and/or decreasing the sampling rate if the patient's activity level is stable over a selected period of time.

In at least another embodiment of the exemplary methods described herein, monitoring one or more physiological parameters of the patient may include monitoring the patient's heart rate, and modifying the sampling rate based on the monitored one or more physiological parameters may include increasing the sampling rate if a change in the patient's heart rate is detected and/or decreasing the sampling rate if the patient's heart rate is stable over a selected period of time.

In at least another embodiment of the exemplary methods described herein, modifying the sampling rate based on the monitored one or more physiological parameters may include determining whether the patient is resting based on the monitored one or more physiological parameters, and modifying the sampling rate based on the monitored one or more physiological parameters may include decreasing the sampling rate if the patient is resting.

In at least another embodiment of the exemplary methods described herein, the exemplary method further includes generating a profile correlating at least one of the monitored one or more physiological parameters to the patient's sampled intrinsic AV conduction time (e.g., the profile may correlate the patient's sampled intrinsic AV conduction time to the patient's heart rate) and modifying the sampling rate based on the profile.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods and devices shall be described with reference to FIGS. 1-6. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or or sizes, or types of elements, may be advantageous over others.

Figure 1:
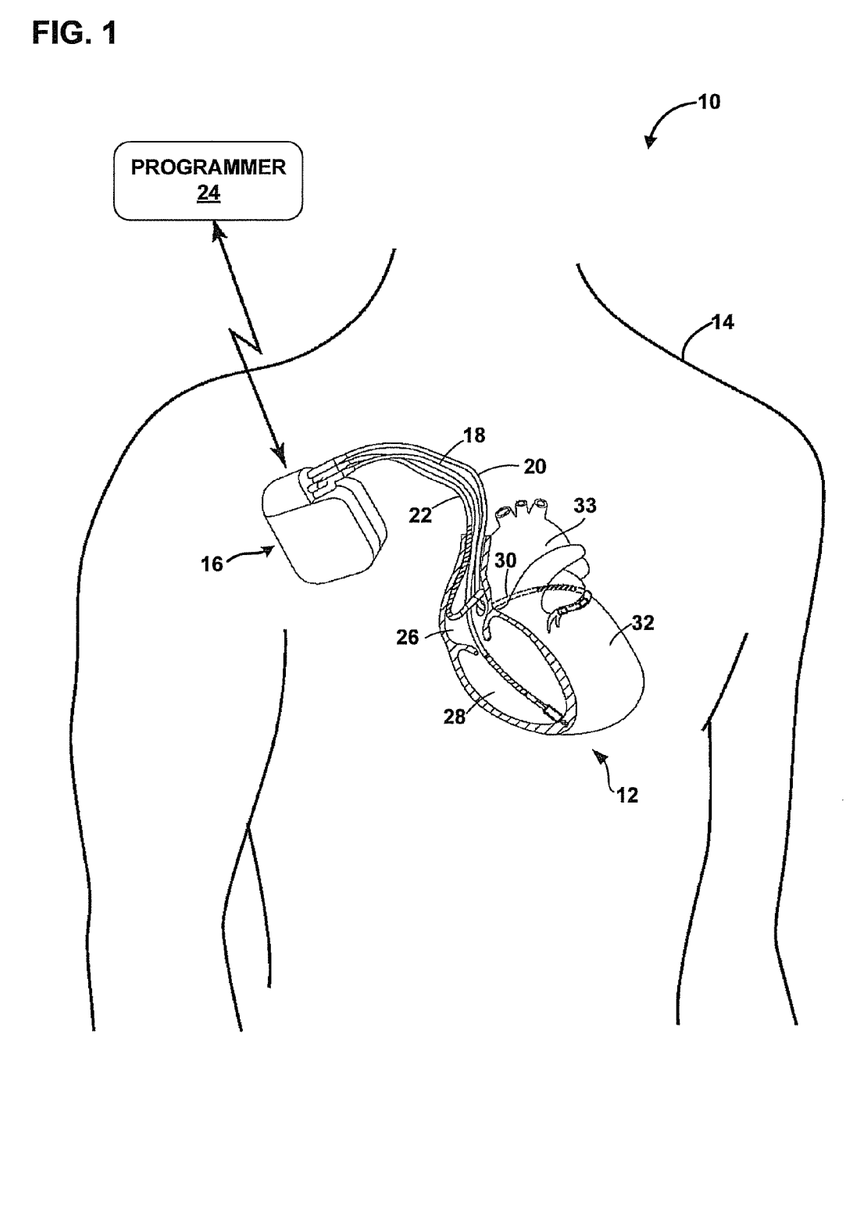
FIG. 1 is a diagram of an exemplary system including an exemplary implantable medical device (IMD).

FIG. 1 is a conceptual diagram illustrating an exemplary therapy system 10 that may be used in the delivery of cardiac therapy and/or in the monitoring, of one or more physiological parameters of a patient 14. Patient 14 may, but not necessarily, be a human. The exemplary therapy system 10 may include an implantable medical device 16 (IMD), which may be coupled to leads 18, 20, 22 and a programmer 24. The IMD 16 may be, e.g., an implantable pacemaker, cardioverter, and/or or defibrillator, that provides electrical signals (e.g., stimulation pulses) to the heart 12 of the patient 14 via electrodes coupled to one or more of the leads 18, 20, 22.

The leads 18, 20, 22 extend into the heart 12 of the patient 14 to sense electrical activity of the heart 12 and/or deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing pulses to the heart 12 based on the electrical signals sensed within the heart 12. The configurations of electrodes used by the IMD 16 for sensing and pacing may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses.

In some examples, the programmer 24 may be a handheld computing device or a computer workstation, which a user, such as a physician, technician, other clinician, and/or patient may use to communicate with the IMD 16. For example, the user may interact with the programmer 24 to retrieve and/or transmit physiological and/or diagnostic information (e.g., one or more physiological parameters, intrinsic AV conduction times, sampling rates, etc.) from the IMD 16.

The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
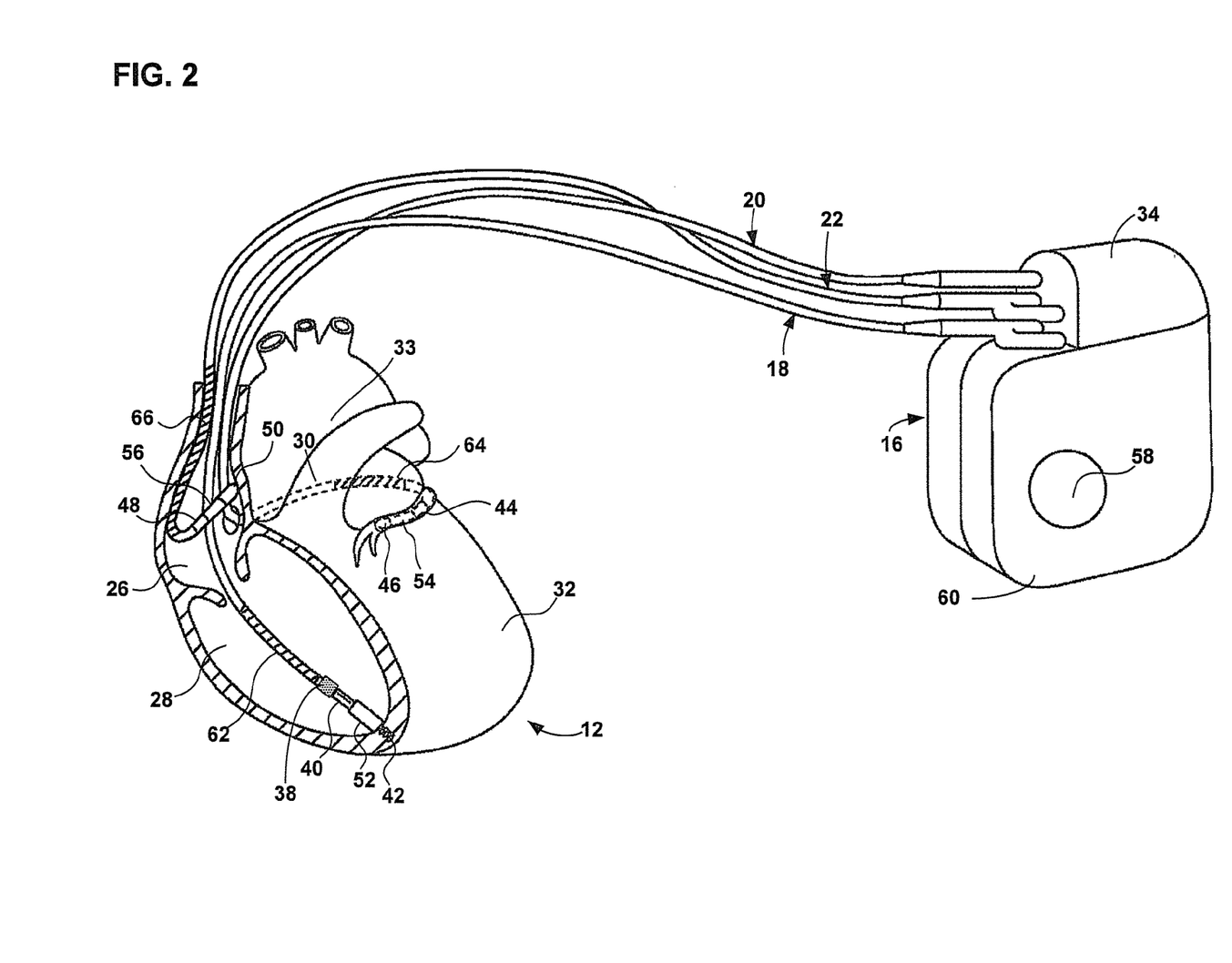
FIG. 2 is a diagram of the IMD of FIG. 1 including leads extending into a patient's heart.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module, a sensing module, and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 may include an elongated insulative lead body, which, e.g., may carry a number of concentric coiled conductors, or straight conductors, separated from one another by insulative material. In the illustrated example, a pressure sensor 38 and bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22. As shown in FIG. 2, the pressure sensor 38 is disposed in the right ventricle 28 of the patient's heart 12. The pressure sensor 38 may respond to an absolute pressure inside the right ventricle 28, and may be, e.g., a capacitive and/or piezoelectric pressure sensor. In other examples, the pressure sensor 38 may be positioned within other regions of the heart 12 (e.g., the left ventricle) and may monitor pressure within one or more of the other regions of the heart 12, or may be positioned elsewhere within or proximate to the cardiovascular system of the patient 14 to monitor cardiovascular pressure associated with mechanical contraction of the heart.

The electrodes 40, 44, 48 may take the form of ring electrodes, and the electrodes 42, 46, 50 may take the faun of extendable helix tip electrodes mounted retractably within the insulative electrode heads 52, 54, 56, respectively. Each of the electrodes 40, 42, 44, 46, 48, 50 may be electrically coupled to a respective one of the coiled conductors within the lead body of its associated lead 18, 20, 22, and thereby coupled to respective one of the electrical contacts on the proximal end of the leads 18, 20, 22.

The electrodes 40, 42, 44, 46, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12 (e.g., for use in CRT). In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66, and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes.

The pressure sensor 38 may be coupled to one or more conductors within the lead 18. In FIG. 2, the pressure sensor 38 is located more distally on the lead 18 than the elongated electrode 62. In other examples, the pressure sensor 38 may be positioned more proximally than the elongated electrode 62, rather than distal to the electrode 62. Further, the pressure sensor 38 may be coupled to another one of the leads 20, 22 in other examples, or to a lead other than the leads 18, 20, 22 carrying stimulation and sense electrodes. In addition, for example, the pressure sensor 38 may be self-contained device that is implanted within the heart 12, such as within the septum separating the right ventricle 28 from the left ventricle 32, or the septum separating the right atrium 26 from the left atrium 33. In such an example, the pressure sensor 38 may wirelessly communicate with a sensing module of the IMD 16.

The configuration of the therapy system 10 illustrated in FIGS. 1-2 is merely one example. In other examples, a therapy system may include epicardial leads and/or patch electrodes instead of, or in addition to, the transvenous leads 18, 20, 22 illustrated in FIG. 1. Further, in one or more embodiments, the IMD 16 may not be implanted within the patient 14. For example, the IMD 16 may deliver defibrillation shocks and other therapies to the heart 12 via percutaneous leads that extend through the skin of the patient 14 to a variety of positions within, or outside of, the heart 12.

In other examples of therapy systems that provide electrical stimulation therapy to the heart 12, a therapy system may include any suitable number of leads coupled to the IMD 16, and each of the leads may extend to any location within or proximate to the heart 12. For example, other examples of therapy systems may include three transvenous leads located as illustrated in FIGS. 1-2, and an additional lead located within or proximate to the left atrium 33. Still further, other therapy systems may include a single lead that extends from the IMD 16 into the right atrium 26 or the right ventricle 28, or two leads that extend into a respective one of the right ventricle 26 and the right atrium 28.

Figure 3:
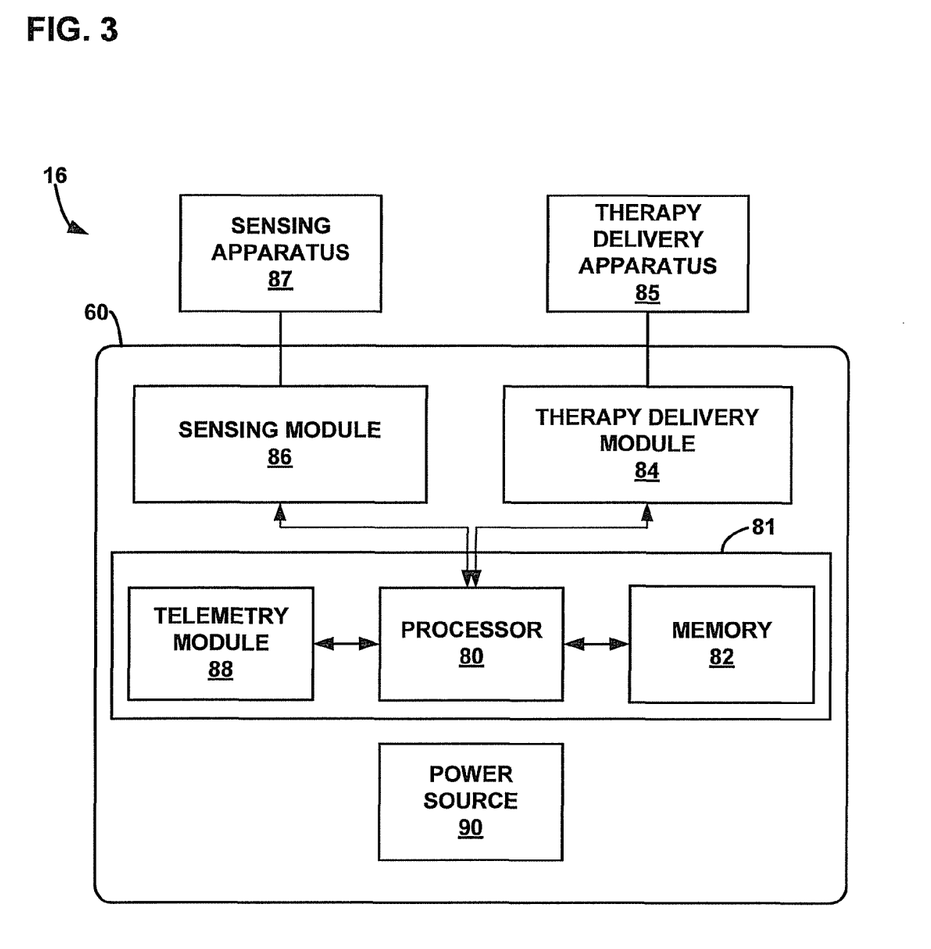
FIG. 3 is a block diagram of the IMD of FIG. 1.

FIG. 3 is a functional block diagram of one exemplary configuration of the IMD 16. As shown, the IMD 16 may include a control module 81, a therapy delivery module 84 (e.g., a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and the control module 81 to perform various functions attributed to the IMD 16 and the control module 81 described herein. Further, the memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor 80 of the control module 81 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 80 herein may be embodied as software, firmware, hardware, or any combination thereof.

The control module 81 controls the therapy delivery module 84 to deliver therapy (e.g., electrical stimulation or pacing therapy) to the heart 12 according to one or more therapy programs, which may be stored in the memory 82. For example, the processor 80 of the control module 81 may control the therapy delivery module 84 to deliver electrical pulses with timings, delays, intervals, amplitudes, pulse widths, frequency, and/or electrode polarities specified by the one or more therapy programs.

Further, at least one therapy program stored in the memory 82 may control the sampling of the patient's intrinsic AV conduction time. For example, an intrinsic AV conduction time sampling rate may be stored in memory 82, such as 1 sample per 1 minute (60 seconds). As described herein in more detail with respect to one or more exemplary embodiments and FIGS. 5-7, the intrinsic AV conduction time sampling rate may be modified based on one or more monitored physiological parameters of the patient 14.

Although not shown, the IMD 16 may further include a notification module that is configured to provide an alert (e.g., to the patient, a clinician, and/or hospital), such as an audio, somatosensory, visual alert, and/or telemetry to an external data collection server. In some cases, the IMD 16 may send the alert to another device, such as the programmer 24, either automatically or upon request. In at least one embodiment, the control module 81 may be configured to initiate an alert using the notification module based on an assessment of one or more conditions of the patient, indications of lead failure, indications of lead dislodgement, etc.

The therapy delivery module 84 is coupled (e.g., electrically coupled) to therapy delivery apparatus 85. The therapy deliver apparatus 85 may include, among other therapy delivery devices, the electrodes 40, 42, 44, 46, 48, 50, 58, 62, 64, 66 of the exemplary systems of FIGS. 1-2 (e.g., via conductors of the respective leads 18, 20, 22) and/or the housing electrode 58. In one or more embodiments, the therapy delivery module 84 may be configured to generate and deliver electrical stimulation therapy to the heart 12. For example, the therapy delivery module 84 may deliver pacing pulses via the ring electrodes 40, 44, 48 coupled to the leads 18, 20, 22, respectively, and/or the helical electrodes 42, 46, 50 of the leads 18, 20, 22, respectively. Further, for example, the therapy delivery module 84 may deliver defibrillation shocks to the heart 12 via at least two of the plurality of electrodes, e.g., electrodes 58, 62, 64, 66. In some examples, the therapy delivery module 84 delivers pacing, cardioversion, and/or defibrillation stimulation in the form of electrical pulses.

The sensing module 86 is coupled (e.g., electrically coupled) to sensing apparatus 87, e.g., to monitor signals from the sensing apparatus 87. The sensing apparatus 87 may include the electrodes 40, 42, 44, 46, 48, 50, 58, 62, 64, 66 to monitor electrical activity of the heart 12, e.g., electrocardiogram (ECG) signals, impedance signals between two or more electrodes (e.g., right and/or left ventricle impedance, subcutaneous impedance, impedance waveform during ejection, impedance waveform during filling, etc.), etc. The ECG signals may be used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as intrinsic AV conductions, P-R intervals, A-V intervals, or P-Q intervals), QRS-complex morphology, ST segment (i.e., the segment that connects the QRS complex and the T-wave), T-wave changes, QT intervals, electrical vectors, etc. The impedance signals may be used to monitor stroke volume (SV), ejection time (ET), etc.

The sensing apparatus 87 may further include one or more pressure sensors, motion/posture sensors (e.g., 2-D and/or 3-D accelerometers), heart sound sensors, activity sensors, perfusion sensors, etc. to monitor one or more heart-related physiological parameters such as, e.g., activity level, posture, ejection time, stroke volume, cardiac output, pre-ejection time, filling time, normalized ejection time % (ejection time divided by the R-R interval expressed as a percentage), etc.

In one or more embodiments, the sensing module 86 and/or the control module 81 may use one or more of the signals collected or monitored by the sensing apparatus 86 to determine a patient's activity level and/or change in activity level. As used herein, a patient's "activity level" may be a value or metric reflective of the amount of activity the patient is undergoing (e.g., physical activity, movement, etc.). For example, exemplary methods and devices may utilize motion sensors (e.g., accelerometers) and/or vibration sensors (e.g., piezoelectric sensors) to determine the activity level of the patient 14.

In at least one embodiment, activity level may be scored or graded within a range with a minimum value representing no or very little activity and a maximum value representing an excessive or inordinate amount of activity. In at least one embodiment, activity level may be monitored by events per second (e.g., deflections of the sensor per second). 0 events per second may indicate that the patient is at rest and 8 events per second may indicate that the patient is at a higher (e.g., maximum) activity level. In at least another embodiment, the amplitude of the signal from an activity sensor may be used to determine activity level (e.g., a relatively large amplitude may indicate a high activity level and a relatively small amplitude may indicate a low activity level).

One example of a sensor capable of detecting patient posture, motion, and activity is an accelerometer, such as a multi-axis accelerometer. A three-axis accelerometer, e.g., may be able to detect motion and posture by detecting acceleration along three axes. An exemplary accelerometer that may be used with the methods and devices disclosed herein may be described in U.S. Pat. No. 5,425,750 to Moberg, which is incorporated by reference in its entirety.

Further, for example, exemplary methods and devices to measure activity level may also utilize sensed breathing patterns using transthoracic impedance, physiologic durations between the Q and T waves (e.g., Vitatron QT rate response), and impedance characteristic measurement on the electrodes in the ventricle (e.g., Biotronik Closed Loop Stimulation (CLS)). Still further, exemplary methods and/or devices that may be used with the methods and devices disclosed herein may be described in U.S. Pat. No. 7,395,113 to Heruth et al., which is incorporated by reference in its entirety.

In at least one embodiment, one channel of the sensing module 86 may include an R-wave amplifier that receives signals from the electrodes 40, 42, which may be used for pacing and sensing in the right ventricle 28 of the heart 12. Another channel may include another R-wave amplifier that receives signals from the electrodes 44, 46, which are used for pacing and sensing proximate to the left ventricle 32 of the heart 12. In some examples, the R-wave amplifiers may take the form of an automatic gain controlled amplifier that provides an adjustable sensing threshold as a function of the measured R-wave amplitude of the heart rhythm.

In addition, in at least one embodiment, one channel of the sensing module 86 may include a P-wave amplifier that receives signals from the electrodes 48, 50, which may be used for pacing and sensing in the right atrium 26 of the heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of the sensing module 86 may be selectively coupled to the housing electrode 58, or the elongated electrodes 62, 64, 66, with or instead of one or more of the electrodes 40, 42, 44, 46, 48, 50, e.g., for unipolar sensing of R-waves or P-waves in any of the chambers 26, 28, 30, 32 of the heart 12.

In some examples, the sensing module 86 may include a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in the memory 82 as an electrogram (EGM). In some examples, the storage of such EGMs in the memory 82 may be under the control of a direct memory access circuit. The processor 80 may employ digital signal analysis techniques to characterize the digitized signals stored in the memory 82 to detect and classify the patient's heart rhythm from the electrical signals. The processor 80 may detect and classify the heart rhythm of the patient 14 by employing any of the numerous signal processing methodologies known in the art.

If the IMD 16 is configured to generate and deliver pacing pulses to the heart 12, the control module 81 (e.g., the processor 80) may include pacer timing and control apparatus, which may be embodied as hardware, firmware, software, or any combination thereof. The pacer timing and control apparatus may comprise a dedicated hardware circuit, such as an ASIC, separate from other processor components, such as a microprocessor, or a software module executed by a component of the processor 80, which may be a microprocessor or ASIC. The pacer timing and control apparatus may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. In the pacing modes, the first letter identifies either a single-chamber (S), dual-chamber (D) or neither-chamber (O) mode, the second letter corresponds to the chamber(s) sensed, the third letter identifies the pacemaker's response to a sensed event—either triggered (T), inhibited (I) or dual (D), and the fourth letter, if any, indicates a rate responsive feature.

Values or variables (e.g., intervals, rates, etc.) defined by the pacer timing and control apparatus within the control module 81 may include intrinsic AV conduction time sampling rates, atrial and ventricular pacing escape intervals, refractory periods during which sensed P-waves and R-waves are ineffective to restart timing of the escape intervals, and the pulse widths of the pacing pulses.

For example, the intrinsic AV conduction time sampling rate is a rate at which the patient's intrinsic AV conduction time is to be measured. As used herein, the intrinsic AV conduction time sampling rate is not zero, i.e., the sampling rate is a positive number such that sampling is occurring. The intrinsic AV conduction time sampling rate may define the amount of samples per time period, e.g., samples per minute (or 60 seconds), or may be defined by the time period or interval between samples, e.g., 60 seconds between samples.

For the purposes of the present disclosure, the intrinsic AV conduction time sampling rate is to be considered in terms of samples per time period (e.g., samples per minute), and as a result, when the sampling rate is described as increasing, it is meant that more samples per time period are to occur, and likewise, when the sampling rate is described as decreasing, it is meant that less samples per time period art to occur. For example, if the intrinsic AV conduction time sampling rate is 1 sample per 1 minute (or 60 seconds), the sampling rate may be described as being increased if the sampling rate is changed to 2 samples per 1 minute, and may be described as being decreased if the sampling rate is changed to 1 sample per 2 minutes (or 120 seconds).

Further, for example, the pacer timing and control apparatus may define a blanking period, and provide signals from the sensing module 86 to blank one or more channels, e.g., amplifiers, for a period during and after delivery of electrical stimulation to the heart 12. The durations of these intervals may be determined by the processor 80 in response to stored data in the memory 82. The pacer timing and control apparatus may also determine the amplitude of the cardiac pacing pulses.

During pacing, escape interval counters within the pacer timing and control apparatus may be reset upon sensing of R-waves and P-waves. The therapy delivery module 84 may include pacer output circuits that are coupled, e.g., selectively by a switching module, to any combination of the electrodes 40, 42, 44, 46, 48, 50, 58, 62, or 66 appropriate for delivery of a bipolar or unipolar pacing pulse to one of the chambers of the heart 12. The processor 80 may reset the escape interval counters upon the generation of pacing pulses by the therapy delivery module 84, and thereby control the basic timing of cardiac pacing functions, including anti-tachyarrhythmia pacing.

In some examples, the control module 81 (e.g., the processor 80) may operate as an interrupt driven device, and may be responsive to interrupts from the pacer timing and control apparatus, where the interrupts may correspond to various intervals (e.g., AV delays, etc.), rates (e.g., intrinsic AV conduction time sampling rate, etc.), cardiac occurrence (e.g., sensed P-waves and R-waves, cardiac pacing pulses, etc.).

Any necessary mathematical calculations to be performed, e.g., by the processor 80 and any updating of the values or intervals controlled by the pacer timing and control apparatus may take place following such interrupts. A portion of the memory 82 may be configured as a plurality of recirculating buffers, capable of holding series of measured intervals, which may be analyzed, e.g., by the processor 80 in response to the occurrence of a pace or sense interrupt to determine whether the patient's heart 12 is presently exhibiting atrial or ventricular tachyarrhythmia.

In at least one embodiment, the IMD 16 may be configured to perform adaptive CRT. Adaptive CRT may be as defined CRT that is automatically optimized based on one or more monitored physiological parameters of the patient 14. One of the monitored physiological parameters that may be used in adaptive CRT is the patient's intrinsic AV conduction time, which, as previously described herein, is the time interval between an atrial event (e.g., in the right atrium) and an intrinsic ventricular event (e.g., in the right ventricle).

In at least one embodiment, if the control module 81 detects an atrial or ventricular tachyarrhythmia based on signals from the sensing module 86, and an anti-tachyarrhythmia pacing regimen is desired, timing intervals for controlling the generation of anti-tachyarrhythmia pacing therapies by the therapy delivery module 84 may be loaded by processor 80 into the pacer timing and control apparatus to control the operation of the escape interval counters therein and to define refractory periods during which detection of R-waves and P-waves is ineffective to restart the escape interval counters.

The telemetry module 88 of the control module 81 may include any suitable hardware, firmware, software, or any combination thereof for communicating with another device, such as the programmer 24 (FIG. 1). For example, under the control of the processor 80, the telemetry module 88 may receive downlink telemetry from and send uplink telemetry to the programmer 24 with the aid of an antenna, which may be internal and/or external to the IMD 16. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

In some examples, the processor 80 may transmit atrial and ventricular heart signals (e.g., electrocardiogram signals) produced by atrial and ventricular sensing circuits within the sensing module 86 to the programmer 24. The programmer 24 may interrogate IMD 16 to receive the heart signals. The processor 80 may store heart signals within the memory 82, and retrieve stored heart signals from the memory 82.

The various components of the IMD 16 may be further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 4:
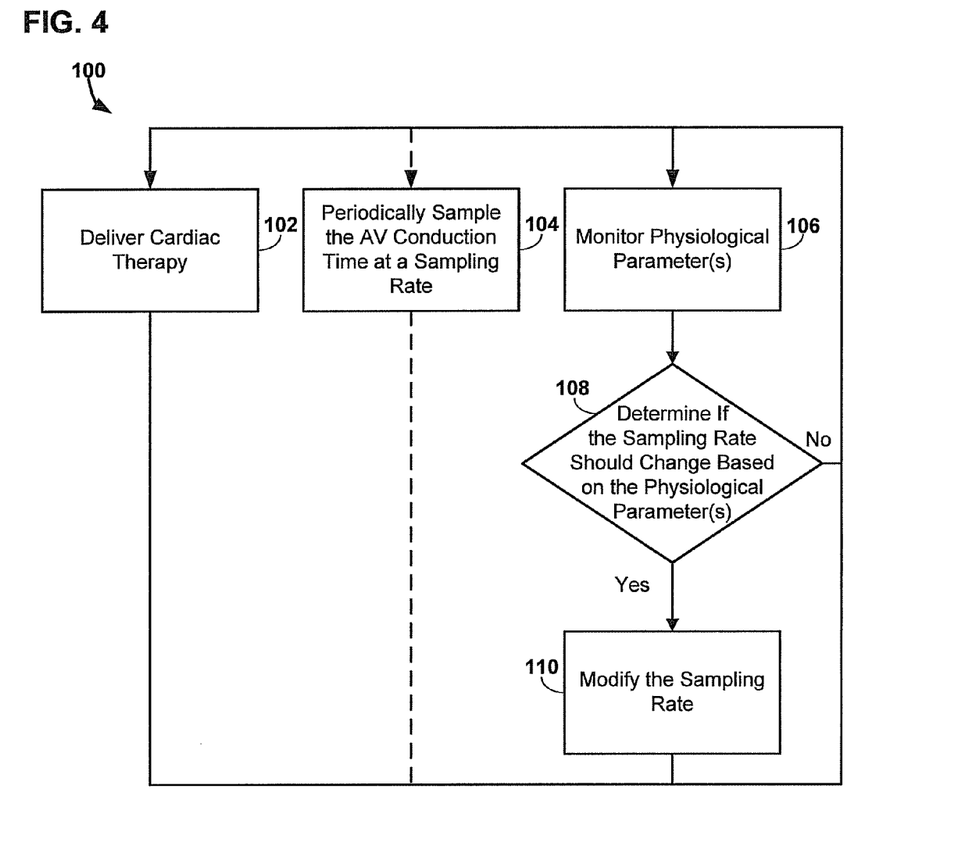
FIG. 4 is a flow chart of an exemplary method for use in delivering cardiac therapy to a patient, e.g., using the IMD of FIGS. 1-3.

A generalized method 100 for use in a medical device (e.g., the implantable medical device of FIGS. 1-3) operable for delivery of cardiac therapy (e.g., CRT) to a patent is diagrammatically depicted in FIG. 4. Method 100 is intended to illustrate the general functional operation of the devices and/or systems described herein, and should not be construed as reflective of a specific form of software or hardware necessary to practice all of the methods described herein. It is believed that the particular form of software will be determined primarily by the particular system architecture employed in the device (e.g., IMD 16) and by the particular detection and therapy delivery methodologies employed by the device and/or system. Providing software and/or hardware to accomplish the described methods in the context of any modern IMD, given the disclosure herein, is within the abilities of one of skill in the art.

The method 100 of FIG. 4 includes delivering cardiac therapy 102 to a patient and monitoring one or more physiological parameters 106 of the patient. The delivered cardiac therapy 102 may include, e.g., adaptive cardiac resynchronization therapy (aCRT). aCRT may use, among other things, the patient's intrinsic AV conduction time to optimize the therapy delivered (e.g., pacing therapy) to the patient's heart. In at least one embodiment, delivering cardiac therapy may include determining an optimal AV delay for use in pacing the patient's heart based on the sampled patient's intrinsic AV conduction time and pacing the patient's heart based on the determined optimal AV delay. More specifically, at least one embodiment of aCRT may utilize a starting offset of 40 ms (e.g., the ventricle may be paced 40 ms prior to intrinsic conduction). If the patient's intrinsic AV conduction time increases beyond 170 ms, then aCRT may be more aggressive and subtract 5 ms from the 40 ms offset for every 10 ms the patient's intrinsic AV conduction time increases beyond 170 ms.

To determine the patient's intrinsic AV conduction time, the method 100 may periodically sample the patient's AV conduction time at a sampling rate 104. As used herein, periodically sampling may be defined as cyclical or recurring sampling, which cycles or recurs at an adjustable sampling rate. In other words, the intrinsic AV conduction time sampling rate used by the exemplary methods and devices described herein may be adjusted or modified "on the fly," e.g., while pacing therapy is being delivered, after an IMD has been implanted in a patient, etc.

To measure the patient's intrinsic AV conduction time, generally, the medical device may delay or cease (e.g., for a single beat) the delivery of cardiac therapy 102 (e.g., ventricular pacing) to provide a time period during which to measure the patient's intrinsic AV conduction time (e.g., forcing the AV delays to fixed long values). The patient, however, may perceive these periodic measurement heart beats and be bothered by how often they occur, and because, prior art devices and methods utilize fixed sampling rates (e.g., a precise time between each measurement such as 60 seconds), the patient may be able to predict and anticipate the next measurement beat, which may increase the level of perception and annoyance by the patient. Further, since a medical device may delay or cease the delivery of cardiac therapy (e.g., ventricular pacing) to measure the patient's intrinsic AV conduction time, the cardiac therapy being delivered to the patient may be disrupted (e.g., become unsynchronized, etc.).

The exemplary method 100 may reduce the patient perception and improve any therapy disruption by modifying or adjusting the sampling rate based on one or more monitored physiological parameters 110 to, e.g., reduce the number of measurements while maintaining the desired response time to adapt to changes in the patient's intrinsic AV conduction time. As described herein, the method 100 may monitor (e.g. continuously monitor) one or more physiological parameters 106 that may be indicative of the patient's intrinsic AV conduction time. The method 100 may use these monitored physiological parameters to determine if the sampling rate should be changed 108.

If it is determined that the intrinsic. AV conduction time sampling rate should not be changed 108, the method 100 may continue delivering cardiac therapy 102, periodically sampling the AV conduction time at the sampling rate 104, and monitoring one or more physiological parameters 106. If it is determined that the intrinsic AV conduction time sampling rate should be changed 108, the method 100 may proceed to modifying the sampling rate 110.

Modifying the intrinsic AV conduction time sampling rate 110 may include increasing or decreasing the sampling rate depending on the monitored one or more physiological parameters 106. The monitored one or more physiological parameters may change, stabilize, increase, and/or decrease, which may provide an indication of whether the patient's intrinsic AV conduction time should be sampled more or less often. For example, changes, stabilizations, increases, and/or decreases in the monitored physiological parameters (e.g., patient's activity level, heart rate, etc.) may indicate the patient's intrinsic AV conduction time may have changed, stabilized, increased, and/or decreased, and as such, the patient's intrinsic AV conduction time may need to be sampled more often (e.g., at least until it is determined that the patient's intrinsic conduction time has stabilized) or less often (e.g., when the patient's intrinsic conduction time has stabilized). In one or more embodiments, the method 100 may determine if the intrinsic AV conduction time sampling rate should change based on the patient's activity level and/or heart rate.

In at least one embodiment, the intrinsic AV conduction time sampling rate may change depending on whether the patient is active or inactive, at rest or not rest, etc. For example, the intrinsic AV conduction time sampling rate may be increase if a monitored physiological parameter has increased and may be decreased if the monitored physiological parameter decreased as shown in FIG. 5.

Figure 5:
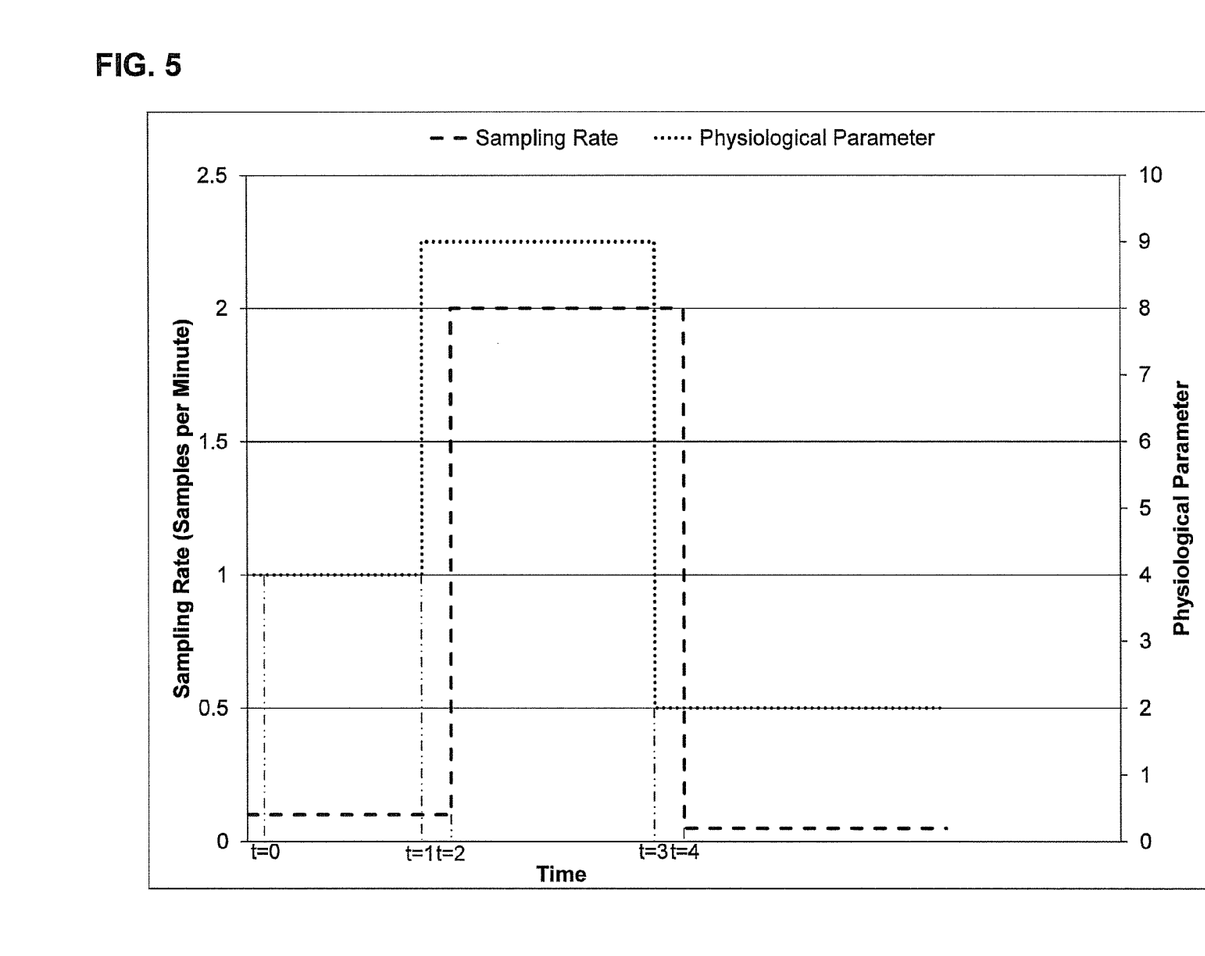
FIG. 5 is a graph displaying a physiological parameter and an intrinsic AV conduction time sampling rate modified using the exemplary method of FIG. 4.

Again, an intrinsic AV conduction time sampling rate and a monitored physiological parameter are plotted over time in FIG. 5. The intrinsic AV conduction time sampling rate is plotted within a range of 0 samples per minute to 2.5 samples per minute, and the monitored physiological parameter is plotted within an arbitrary range of 0 to 10 with 0 representing a low value for the physiological parameter and 10 representing a high value for the physiological parameter.

As shown in FIG. 5, the intrinsic AV conduction time sampling rate is 0.1 samples per minute (or 1 sample per 10 minutes) and the monitored physiological parameter is a value of 4 from t=0 to t=1. At t=1, the monitored physiological parameter increases before stabilizing at a value of 9. The period after t=1 until t=3 may represent a period of high activity.

As the monitored physiological parameter increases, it may be determined that the intrinsic AV conduction time sampling rate should increase accordingly, and the sampling rate may increase to 2 samples per minute at t=2. At t=3, the monitored physiological parameters decreases before stabilizing at a value of 2. The period after t=3 may represent a period of rest. Accordingly, the sampling rate is decreased to 0.05 samples per minute (or 1 sample per 20 minutes) at t=4.

The periods from t=1 to t=2 and t=3 to t=4 may represent selected periods of time in which a change in the monitored physiological parameter is determined (e.g., response times representing the amount of time it may take to react to change). For example, the average of the monitored physiological parameter over the selected period of time and the average of the same monitored physiological parameter of a previous selected period of time may be compared to detect a change.

In other words, the sampling rate increases and decreases (e.g., linearly, proportionally, etc.) according to the monitored physiological parameter as shown in FIG. 5. In one or more embodiments, the monitored physiological parameter may be activity level and/or heart rate.

For example, if the patient's activity level is at relatively high level (e.g., exercise), then the method 100 may increase the intrinsic AV conduction time sampling rate to a relatively high level (e.g., 2 samples per 1 minute), and likewise, if the patient's activity level is at a relatively low rate (e.g., rest), then method 100 may decrease the intrinsic AV conduction time sampling rate to a relatively low rate (e.g., 1 sample per 2 minutes, 1 sample per 5 minutes, 1 sample per 15 minutes, 1 sample per 30 minutes, 1 sample per 1 hour, 1 sample per 2 hours, etc.). Further, for example, if the patient's heart rate has increased to a relatively high level (e.g., 120 beats per minute), the method 100 may increase the intrinsic AV conduction time sampling rate to a relatively high rate (e.g., 2 samples per 1 minute), and likewise, if the patient's heart rate has decreased to a relatively low level (e.g., 50 beats per minute), the method 100 may decrease the intrinsic AV conduction time sampling rate to a relatively low rate (e.g., 1 sample per 2 minutes, 1 sample per 5 minutes, 1 sample per 15 minutes, 1 sample per 30 minutes, 1 sample per 1 hour, 1 sample per 2 hours, etc.).

In at least one embodiment, the sampling rate may increase if the monitored physiological parameter changes and may decrease if monitored physiological parameter has stabilized. Change and stabilization of a monitored physiological parameter may be determined over a selected time period (or selected period of time). The selected time period may be, e.g., more than or equal to about 5 seconds, about 7 seconds, about 10 seconds, about 15 seconds, about 20 seconds, about 25 seconds, about 30 seconds, about 40 seconds, about 50 seconds, about 60 seconds, about 75 seconds, about 100 seconds, about 120 seconds, about 150 seconds, about 180 seconds, and less than or equal to about 15 seconds, about 20 seconds, about 25 seconds, about 30 seconds, about 40 seconds, about 50 seconds, about 60 seconds, about 75 seconds, about 100 seconds, about 120 seconds, about 150 seconds, about 180 seconds, about 5 minutes, about 7 minutes, about 10 minutes, etc.

For example, the physiological parameter may be monitored for about 60 seconds, and the average, median, and/or any another statistical metric of the physiological parameter may be used to determine if the physiological parameter has changed or stabilized since the previous selected time period. For example, the average of the monitored physiological parameter over 30 seconds may be compared to the average of the same monitored physiological parameter over the previous 30 seconds.

Further, change and stabilization of a monitored physiological parameter may be determined using a threshold value representative of change and/or stabilization. The threshold value may be in the form of a percentage, and may be, e.g., more than or equal to and/or less than or equal to about 1%, about 2%, about 5%, about 8%, about 10%, about 15%, about 20%, about 25%, about 30%, about 35%, about 40%, about 50%, about 60%, about 70%, about 80%, about 90%, about 100%, about 125%, about 150%, about 200%, etc.

For example, the threshold value for change may be 20%, and it may be determined that the physiological parameter has changed if the physiological parameter has changed at least 20% from its previous value (e.g., a previous value determined in a previous time period). For instance, if the average of the monitored physiological parameter over 30 seconds has changed at least 20% from the average of the same monitored physiological parameter over the previous 30 seconds, then it may be determined that the monitored physiological parameter has changed.

Likewise, for example, the threshold value for stabilization may also be 20%, and it may be determined that the physiological parameter has stabilized if the physiological parameter has not changed more than 20% from its previous value (e.g., a previous value determined in previous time period). For instance, if the average of the monitored physiological parameter over 30 seconds has not changed more than 20% from the average of the same monitored physiological parameter over the previous 30 seconds, then it may be determined that the monitored physiological parameter has stabilized.

Figure 6:
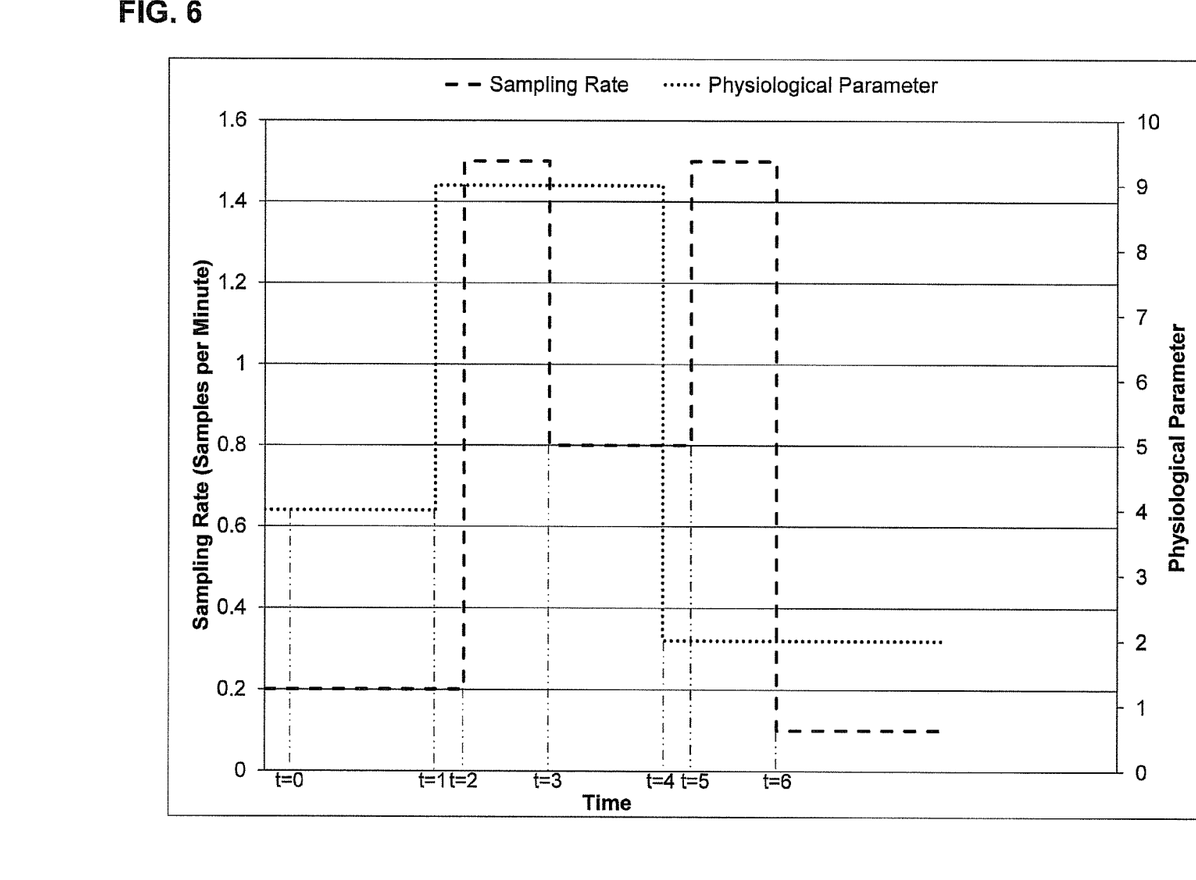
FIG. 6 is another graph displaying a physiological parameter and an intrinsic AV conduction time sampling rate modified using the exemplary method of FIG. 4.

An intrinsic AV conduction time sampling rate and a monitored physiological parameter are plotted over time in FIG. 6 to visualize modification of the intrinsic AV conduction time sampling rate based on change in a physiological parameter (e.g., activity level, heart rate, etc.). As shown, the intrinsic AV conduction time sampling rate is plotted within a range of 0 samples per minute to 1.6 samples per minute, and the monitored physiological parameter is plotted within an arbitrary range of 0 to 10 with 0 representing a low value for the physiological parameter and with 10 representing a high value for the physiological parameter.

As shown in FIG. 6, the intrinsic AV conduction time sampling rate is 0.2 samples per minute (or 1 sample per 5 minutes) and the monitored physiological parameter is a value of 4 (e.g., the patient may be awake and alert and exerting a relatively low amount of energy) from t=0 to t=1. At t=1, the monitored physiological parameter increases before stabilizing at a value of 9 (e.g., the patient may be exerting an increased amount of energy such as through exercise). After it is determined that the monitored physiological parameter has changed, the sampling rate increases accordingly to 1.5 samples per minute at t=2. At t=3, it may have been determined that the monitored physiological parameter has stabilized, and as such, the sampling rate decreases to 0.8 samples per minute.

The period from t=1 to t=2 may represent a selected period of time in which a change in the monitored physiological parameter is determined (e.g., a response time in which to react to the change), and the period from t=2 to t=3 may represent a selected period of time in which stabilization of the monitored physiological parameter is determined (e.g., a response time in which to react to the stabilization). For example, the average of the monitored physiological parameter over the selected period of time and the average of the same monitored physiological parameter of a previous selected period of time may be compared to detect a change or stabilization.

At t=4, the monitored physiological parameter decreases before stabilizing at a value of 2 (e.g., the patient may be at rest). Again, after it is determined that the monitored physiological parameter has changed, the sampling rate increases accordingly to 1.5 samples per minute at t=5. Also, after it has been determined that the monitored physiological parameter has stabilized at t=6, the sampling rate decreases back to 0.1 samples per minute.

In other words, the intrinsic AV condition time sampling rate may increase when the monitored physiological parameter changes and may decrease when it is determined that the monitored physiological parameter has stabilized.

For example, if the patient's activity level changes, the method 100 may increase the intrinsic AV conduction time sampling rate, and likewise, if the patient's activity level is stable, the method 100 may decrease the intrinsic AV conduction time sampling rate. Activity level may be monitored over a period of time (e.g., about 2 seconds, about 3 seconds, about 5 seconds, about 7 seconds, about 10 seconds, about 15 seconds, about 30 seconds, about 60 seconds, about 2 minutes, etc.) and the average, or any other statistical metric, of the activity level over the time period may be used to determine whether to modify the intrinsic AV conduction time sampling rate. As described herein, activity level may be determined through the use of motion sensors (e.g., accelerometers), vibration sensors (e.g., piezoelectric sensors), breathing patterns (e.g., using thoracic impedance), EGM signals (e.g., duration between Q and T waves), impedance characteristics on the electrodes in the ventricle, etc.

Further, for example, if the patient's heart rate changes, the method 100 may increase the intrinsic AV conduction time sampling rate, and likewise, if the patient's heart rate is stable, the method 100 may decrease the intrinsic AV conduction time sampling rate. Like monitoring activity level, the heart rate may be monitored over a period of time (e.g., 30 seconds, 60 seconds, 2 minutes, etc.) and the average, or any other statistical metric, of the heart rate over the time period may be used to determine whether to modify the intrinsic AV conduction time sampling rate.

As shown in FIG. 6, the sampling rate used after the physiological parameter has been determined to be stabilized may also be adjusted based on the monitored physiological parameter (e.g., as described herein with reference to FIG. 5). For example, the sampling at t=3 is greater than the sampling rate at t=6 because the activity level is higher at t=3 then at t=6. In effect, the method described in reference to FIG. 5 is combined with the method described within FIG. 6. In at least another embodiment, the sampling rate may be at a relatively high rate during a period of change and at a relatively low rate during a period of stabilization, regardless of the level of physiological activity.

The exemplary methods 100 may further include processes that measure or sample the patient's intrinsic AV conduction time less often but also build up or generate a patient profile (e.g., within an IMD) that maps at least one of the patient's monitored physiological parameters (e.g., heart rate, activity level, etc.) to intrinsic AV intervals, and then may use this profile to pace the patient's heart and/or modify the intrinsic AV conduction time sampling rate.

For example, the method 100 may further include generating a profile correlating at least one of the monitored one or more physiological parameters to the patient's sampled intrinsic AV conduction time. Since the profile would contain data correlating physiological parameters to the patient's intrinsic AV conduction time, the profile may then be used to pace the patient's heart according to the profile and/or modify the intrinsic AV conduction time sampling rate. In at least one embodiment, the patient's intrinsic AV conduction time may be sampled, and then compared to the profile. If the sampled intrinsic AV conduction time and at least one of the monitored one or more physiological parameters correlate in the profile (e.g., indicating that the monitored physiological parameter may be used in place of an actual sampled AV conduction time for a selected time period), then the profile may be used to pace the patient's heart and/or modify the intrinsic AV conduction time sampling rate (e.g., decrease the sampling rate). Further, if the sampled intrinsic AV conduction time and at least one of the monitored one or more physiological parameters do not correlate in the profile, then it may be determined that the profile may not be used to pace the patient's heart, and it may be determined that the intrinsic AV conduction time sampling rate should be increased (e.g., the lack of a correlation may indicate an anomaly or a problem that may prompt additional sampling). In other words, in this embodiment, before the profile may be used to pace the patient's heart and/or modify the intrinsic AV conduction time sampling rate, the profile may be confirmed (e.g., by "double checking" that the patient's sampled AV conduction time and at least one physiological parameter correlate).

In at least another embodiment, the data within the profile may be compared to the presently monitored physiological parameter to indicate or provide an estimate of the patient's intrinsic AV conduction time without actually sampling the patient's intrinsic AV conduction time. The indication or estimation of the patient's intrinsic AV conduction time may be used to pace the patient's heart and/or increase or decrease the intrinsic AV conduction time sampling rate.

In other words, the profile may be used to establish an estimate or surrogate of the patient's sampled intrinsic AV conduction time, and modify or adjust the cardiac therapy (e.g., to adjust an optimal AV delay) in view of the estimate or surrogate of the patient's intrinsic AV conduction time.

The methods and/or techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An implantable medical device for use in delivering cardiac therapy to a patient comprising:
    sensing apparatus configured to monitor physiological parameters of the patient, wherein the sensing apparatus comprises at least one electrode to monitor electrical activity of the patient's heart;
    a therapy delivery module configured to deliver cardiac therapy to the patient; and
    a control module coupled to the sensing apparatus and to the therapy delivery module and configured to:
        monitor one or more physiological parameters of the patient,
        perform an intrinsic atrioventricular (AV) conduction time measurement on the patient at a measurement rate for use in determining one or more pacing parameters, and
        modify the measurement rate based on the monitored one or more physiological parameters.

2. The device of claim 1, wherein the device further comprises therapy apparatus coupled to the therapy delivery module and configured to deliver cardiac therapy to the patient, wherein the control module is further configured to:
    determine an optimal AV delay for use in pacing the patient's heart based on the patient's measured intrinsic AV conduction time, and
    pace the patient's heart using the therapy apparatus based on the determined optimal AV delay.

3. The device of claim 1, wherein the control module is further configured to:
    determine the patient's activity level based on the monitored one or more physiological parameters, and
    increase the measurement rate if a change in the patient's activity level is detected.

4. The device of claim 3, wherein the control module is further configured to decrease the measurement rate if the patient's activity level is stable over a selected period of time.

5. The device of claim 3, wherein the control module is further configured to:
    monitor the patient's motion, and
    determine the patient's activity level based at least on the patient's motion monitored over a selected period of time.

6. The device of claim 1, wherein the control module is further configured to:
    monitor the patient's heart rate, and
    increase the measurement rate if a change in the patient's heart rate is detected.

7. The device of claim 6, wherein the control module is further configured to decrease the s measurement rate if the patient's heart rate is stable over a selected period of time.

8. The device of claim 1, wherein the control module is further configured to:
    determine whether the patient is resting based on the monitored one or more physiological parameters, and
    decrease the measurement rate if the patient is resting.

9. The device of claim 1, wherein the control module is further configured to:
    generate a profile correlating at least one of the monitored one or more physiological parameters to the patient's measured intrinsic AV conduction time, and
    modify the measurement rate based on the profile.

10. The device of claim 9, wherein the profile correlates the patient's measured intrinsic AV conduction time to the patient's heart rate.

11. A method for use in an implantable medical device operable for delivery of cardiac therapy to a patient, the method comprising:
    monitoring one or more physiological parameters of the patient;

performing an atrioventricular (AV) conduction time measurement on the patient at a measurement rate for use in determining one or more pacing parameters; and modifying the measurement rate based on the monitored one or more physiological parameters.

12. The method of claim 11, wherein the method further comprises:

determining an optimal AV delay for use in pacing the patient's heart based on the patient's measured intrinsic AV conduction time, and pacing the patient's heart based on the determined optimal AV delay.

13. The method of claim 11, wherein modifying the measurement rate based on the monitored one or more physiological parameters comprises:

determining the patient's activity level based on the monitored one or more physiological parameters, and increasing the measurement rate if a change in the patient's activity level is detected.

14. The method of claim 13, wherein modifying the measurement rate based on the monitored one or more physiological parameters further comprises decreasing the measurement rate if the patient's activity level is stable over a selected period of time.

15. The method of claim 13, wherein monitoring one or more physiological parameters of the patient comprises monitoring the patient's motion, and wherein determining the patient's activity level is based at least on the patient's motion monitored over a selected period of time.

16. The method of claim 11, wherein monitoring one or more physiological parameters of the patient comprises monitoring the patient's heart rate, and wherein modifying the measurement rate based on the monitored one or more physiological parameters comprises increasing the measurement rate if a change in the patient's heart rate is detected.

17. The method of claim 16, wherein modifying the measurement rate based on the monitored one or more physiological parameters further comprises decreasing the measurement rate if the patient's heart rate is stable over a selected period of time.

18. The method of claim 11, wherein modifying the measurement rate based on the monitored one or more physiological parameters comprises:

determining whether the patient is resting based on the monitored one or more physiological parameters, and decreasing the measurement rate if the patient is resting.

19. The method of claim 11, wherein the method further comprises:

generating a profile correlating at least one of the monitored one or more physiological parameters to the patient's measured intrinsic AV conduction time, and modifying the measurement rate based on the profile.

20. The method of claim 19, wherein the profile correlates the patient's measured intrinsic AV conduction time to the patient's heart rate.

* * * * *